US009549674B2

(12) United States Patent
Broome et al.

(10) Patent No.: US 9,549,674 B2
(45) Date of Patent: Jan. 24, 2017

(54) METHOD AND DEVICE FOR ESTIMATING A MYOCARDIAL PERFORMANCE PARAMETER

(71) Applicant: ST. JUDE MEDICAL AB, Jarfalla (SE)

(72) Inventors: Michael Broome, Ekero (SE); Andreas Blomqvist, Taby (SE)

(73) Assignee: ST. JUDE MEDICAL AB, Farfalla (SE)

(*) Notice: Subject to any disclaimer, the term of this patent is extended or adjusted under 35 U.S.C. 154(b) by 0 days.

(21) Appl. No.: 14/963,120

(22) Filed: Dec. 8, 2015

(65) Prior Publication Data
US 2016/0089037 A1 Mar. 31, 2016

Related U.S. Application Data

(62) Division of application No. 13/002,599, filed as application No. PCT/SE2008/000483 on Aug. 28, 2008, now Pat. No. 9,241,653.

(51) Int. Cl.
A61N 1/365 (2006.01)
A61B 5/02 (2006.01)
A61B 5/053 (2006.01)
A61B 5/00 (2006.01)
A61N 1/368 (2006.01)

(52) U.S. Cl.
CPC ........... A61B 5/02028 (2013.01); A61B 5/053 (2013.01); A61B 5/0538 (2013.01); A61B 5/686 (2013.01); A61B 5/6846 (2013.01); A61B 5/7239 (2013.01); A61N 1/3682 (2013.01); A61N 1/36521 (2013.01); A61B 5/7235 (2013.01)

(58) Field of Classification Search
CPC A61N 1/36521; A61N 1/0538; A61N 1/3627; A61B 5/02028; A61B 5/053
See application file for complete search history.

(56) References Cited

U.S. PATENT DOCUMENTS 5,417,717 A * 5/1995 Salo ................... A61N 1/36585
607/18
2004/0172079 A1 9/2004 Chinchoy
2005/0228454 A1 10/2005 Kramer et al.
2006/0020294 A1 1/2006 Brockway et al.
(Continued)

FOREIGN PATENT DOCUMENTS

EP 1484083 A1 12/2004

OTHER PUBLICATIONS

Pellett, Andrew A. PhD, R.D.C.S. et al., "The Tei Index: Methodology and Disease State Values," Echocardiography 2004;21(7):669-672.
(Continued)

Primary Examiner — Michael D Abreu

(57) ABSTRACT

An implantable medical device applies an electric signal to at least a portion of a heart in a subject. A resulting electric signal is collected from the heart and is used together with the applied signal for determining a cardiogenic impedance signal. The impedance signal is processed in order to estimate an isovolumetric contraction time, an isovolumetric relaxation time and an ejection time for a heart cycle. These three time parameters are employed for calculating a Tei-index of the heart. The Tei-index can be used as myocardial performance parameter in heart diagnosis and/or cardiac therapy adjustment.

8 Claims, 9 Drawing Sheets

(56) References Cited

U.S. PATENT DOCUMENTS

| | | |
|---|---|---|
| 2006/0167514 A1 | 7/2006 | Kjellstrom et al. |
| 2007/0191901 A1* | 8/2007 | Schecter .............. A61N 1/3627 607/17 |
| 2008/0103539 A1 | 5/2008 | Stegemann et al. |

OTHER PUBLICATIONS

Soliman, Osama I.I. MD, PhD et al., "Predictors of Cardiac Events After Cardiac Resynchronization Therapy with Tissue Doppler-Derived Parameters," J Cardiac Fail. 2007;13:805-811.

Tei, Chuwa MD, "New Non-Invasive Index for Combined Systolic and Diastolic Ventricular Function," J Cardiol. 1995;26:135-136.

Restriction Requirement, mailed Jun. 22, 2012—U.S. Appl. No. 13/002,599.

NonFinal Office Action, mailed Jul. 12, 2013—U.S. Appl. No. 13/002,599.

Final Office Action, mailed Feb. 11, 2014—U.S. Appl. No. 13/002,599.

Advisory Action, mailed Jun. 5, 2014—U.S. Appl. No. 13/002,599.

NonFinal Office Action, mailed Mar. 30, 2015—U.S. Appl. No. 13/002,599.

Notice of Allowance, mailed Oct. 7, 2015—U.S. Appl. No. 13/002,599.

* cited by examiner

METHOD AND DEVICE FOR ESTIMATING A MYOCARDIAL PERFORMANCE PARAMETER

CROSS REFERENCE TO RELATED APPLICATIONS

This application is a division of U.S. patent application Ser. No. 13/002,599, filed Jan. 4, 2011, which is a 371 application of PCT/SE08/00483, filed Aug. 28, 2008.

FIELD OF THE INVENTION

The present invention generally relates to implantable medical devices and methods, and in particular to such devices and methods employed for estimating a myocardial performance parameter useful for heart diagnosis and adjustment of device settings.

BACKGROUND OF THE INVENTION

Heart failure is a common disease with a prevalence of approximately 2-3 percent in the general population. The disease has a huge impact both on health economy and the well-being of people in western society. Cardiac Resynchronization Therapy (CRT) is an established method to treat heart failure in patients with low ejection fraction and widened QRS-complex. The optimal method to monitor the effects of CRT is however under debate. CRT has important effects on both systolic and diastolic cardiac function. Heart failure affects both systolic and diastolic function.

There is therefore a need for a diagnostic parameter that is descriptive of changes both in diastolic and systolic cardiac properties and which can be used, among others, as control parameter for CRT optimization.

Furthermore, the parameter should be determinable by an implantable medical device, such as pacemaker, defibrillator or cardioverter, having functionality for providing the cardiac resynchronization therapy to the heart failure patient.

A vast number of diagnostic parameters have been used in the art for optimizing CRT of an implantable medical device, such as maximum ventricular $$\frac{dP}{dt}$$

using a ventricular pressure sensor (1), heart sound measurements (2), a map of conduction time between multiple heart sites (3), stroke volume derived from blood pressure in the aorta (4) and left ventricular lateral wall acceleration (5).

These prior art parameters and implantable medical devices typically require dedicated sensor equipment, such as pressure sensors, acoustic sensors, acceleration sensors, resulting in more complex devices and more problematic implantation of the devices.

Furthermore, not all prior art parameters are indeed particularly suitable as CRT optimization parameters as they are not descriptive of changes both in diastolic and systolic cardiac properties.

SUMMARY OF THE INVENTION

There is therefore a need for a myocardial performance parameter that can effectively be used in heart diagnosis and heart treatment optimization, and which furthermore can be estimated without the requirement of separate, dedicated sensors attached to implantable medical devices.

The present invention overcomes these and other drawbacks of the prior art arrangements.

It is a general object of the present invention to determine a myocardial performance parameter from cardiac impedance data.

It is a particular object of the invention to provide an implantable medical device capable of determining a Tei-index without dedicated, included or attached sensor equipment.

Briefly, the present invention concerns an implantable medical device (IMD) designed for monitoring and/or applying therapy to a heart of a patient, preferably mammalian patient and more preferably a human patient. The IMD has an electrode input connectable to multiple implantable electrodes preferably attached to one or more cardiac leads connectable to the IMD. A signal generator is electrically connected to the electrode input and generates an electric signal, preferably AC current signal, which is applied to at least a portion of the heart using two of the connected electrodes. A resulting electric signal, preferably AC voltage signal, is collected from at least a portion of the electrode using two connected electrodes.

The IMD has an impedance processor that determines an impedance signal, typically cardiogenic impedance signal, based on the applied electric signal and the collected resulting electric signal. This impedance signal is processed by different time processors of the IMD for the purpose of determining time parameters. An isovolumetric contraction time (IVCT) processor estimates an IVCT of a heart cycle based on the impedance signal. An isovolumetric relaxation time (IVRT) is correspondingly estimated by an IVRT processor from the impedance signal during the heart cycle. An ejection time (ET) processor estimates the ET of the heart cycle based on the impedance signal.

The IMD also includes an index processor that determines the myocardial performance parameter denoted Tei-index in the art based on the estimated IVCT, IVRT and ET. Thus, the Tei-index can be determined by the IMD based solely on impedance data collected by implanted electrodes connected to the IMD and therefore without the need for separate and dedicated implanted sensors.

The Tei-index is of high diagnostic value as it accounts for changes in both diastolic and systolic cardiac performance. The index can therefore be used as diagnostic parameter for the purpose of detecting a deterioration of myocardial function such as occurring in connection with a heart failure event. The Tei-index can also be used, since it is reflective of the myocardial performance, for adjusting the cardiac therapy delivered by the IMD to the heart. For instance, adjustment or optimization of CRT is advantageously conducted in a biventricular IMD based on the estimated Tei-index.

The present invention also relates to a method of determining the Tei-index based on impedance data determined from electric signals applied to and collected from the heart using implantable electrodes.

BRIEF DESCRIPTION OF THE DRAWINGS

FIG. 3 is a schematic block diagram of an embodiment of the impedance processor of the implantable medical device in FIG. 2.

DESCRIPTION OF THE PREFERRED EMBODIMENTS

Figure 1:
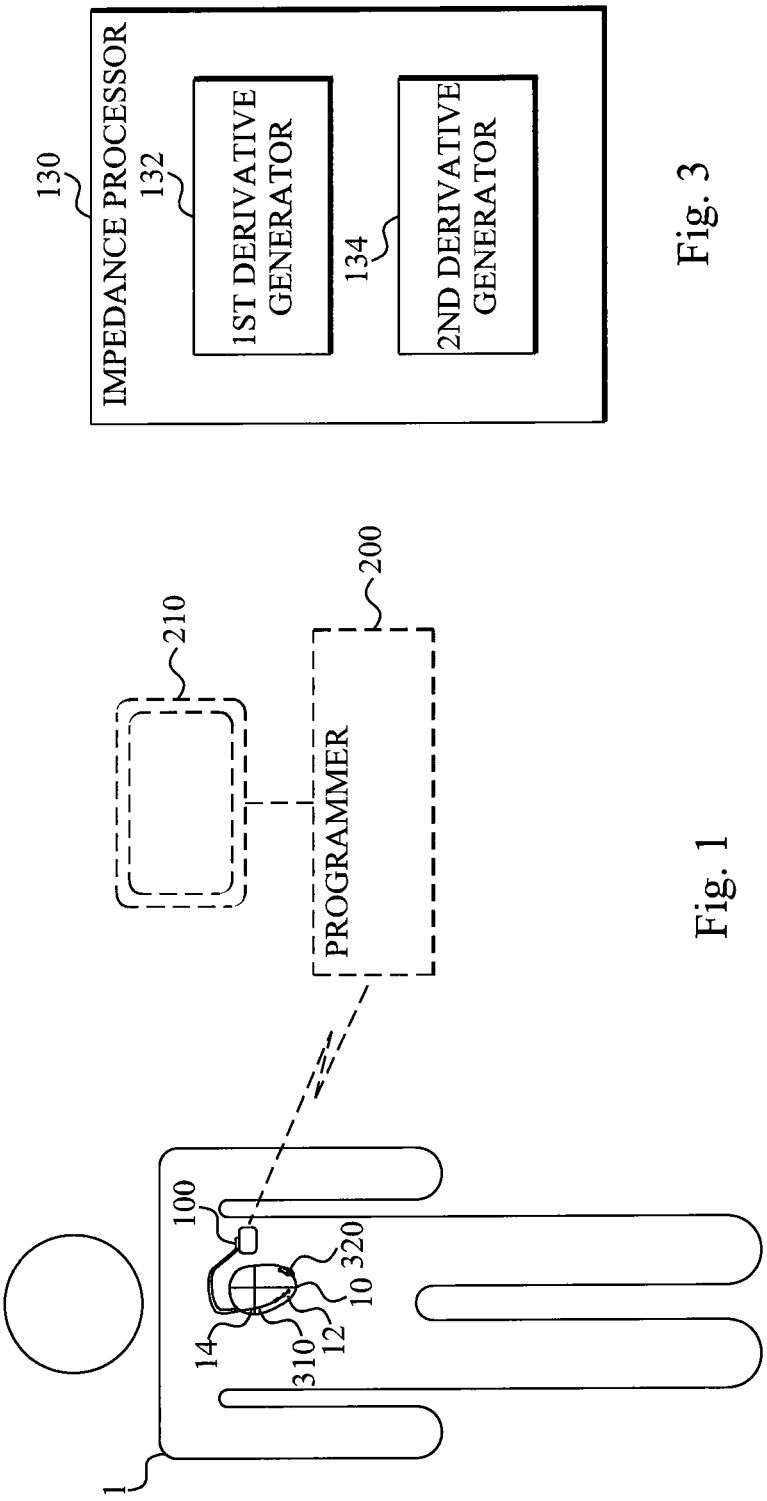
FIG. 1 is an overview of a patient having an implantable medical device according to an embodiment and further illustrates wireless communication between the device and an external terminal.

Throughout the drawings, the same reference characters will be used for corresponding or similar elements.

The present invention is related to an implantable medical device and method that allows estimation of a myocardial performance parameter that is highly descriptive of heart performance, including both diastolic and systolic cardiac performance. As a consequence, the parameter can be used as an effective diagnostic parameter for monitoring heart performance and status and thereby detect any significant changes in the heart operation indicative of a disease condition, such as heart failure, and/or a worsening of an already detected disease condition. Furthermore, the performance parameter can, according to the invention, be used in adjusting and optimizing the operation of the implantable medical device, for instance through an adjustment of the device settings employed for delivering a treatment pacing to combat the detected disease condition.

The performance parameter employed by the invention is the co-called Tei-index, also denoted Myocardial Performance Index, in the art (6). Traditionally, the Tei-index is determined through usage of several different non-invasive sensors. However, the present invention teaches that the Tei-index can surprisingly be estimated through processing of a single parameter signal that can be recorded by the device without the need for any dedicated implantable sensors in or attached to the device. Thus, the invention relates to the usage of an impedance signal, in particular a cardiogenic impedance signal for estimating the myocardial performance parameter, Tei-index.

FIG. 1 is a schematic overview of a human patient 1 having an implantable medical device, IMD, 100 according to the present invention. In the figure, the IMD 100 is illustrated as a device that monitors and/or provides therapy to the heart 10 of the patient 1, such as a pacemaker, cardiac defibrillator or cardioverter. The IMD 100 is, in operation, connected to one or more, two in the figure, intracardiac leads 310, 320 inserted into different heart chambers, the right and left ventricles 12 in FIG. 1. The present invention is though not limited to ventricular leads 310, 320 but can also be used in connection with leads positioned in the right or left atrium 14 of the heart 10. Actually, also non-intracardiac leads, including epicardial leads can also be used.

FIG. 1 also illustrates an external programmer or clinician's workstation 200 that can communicate with the IMD 100. As is well known in the art, such a programmer 200 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 200 before display to a clinician on a connected display screen 210. In the light of the present invention, such uploaded data can include the estimated Tei-index determined by the IMD 100, other diagnostic data determined based on the Tei-index and/or device setting information adjusted based on the Tei-index.

Figure 2:
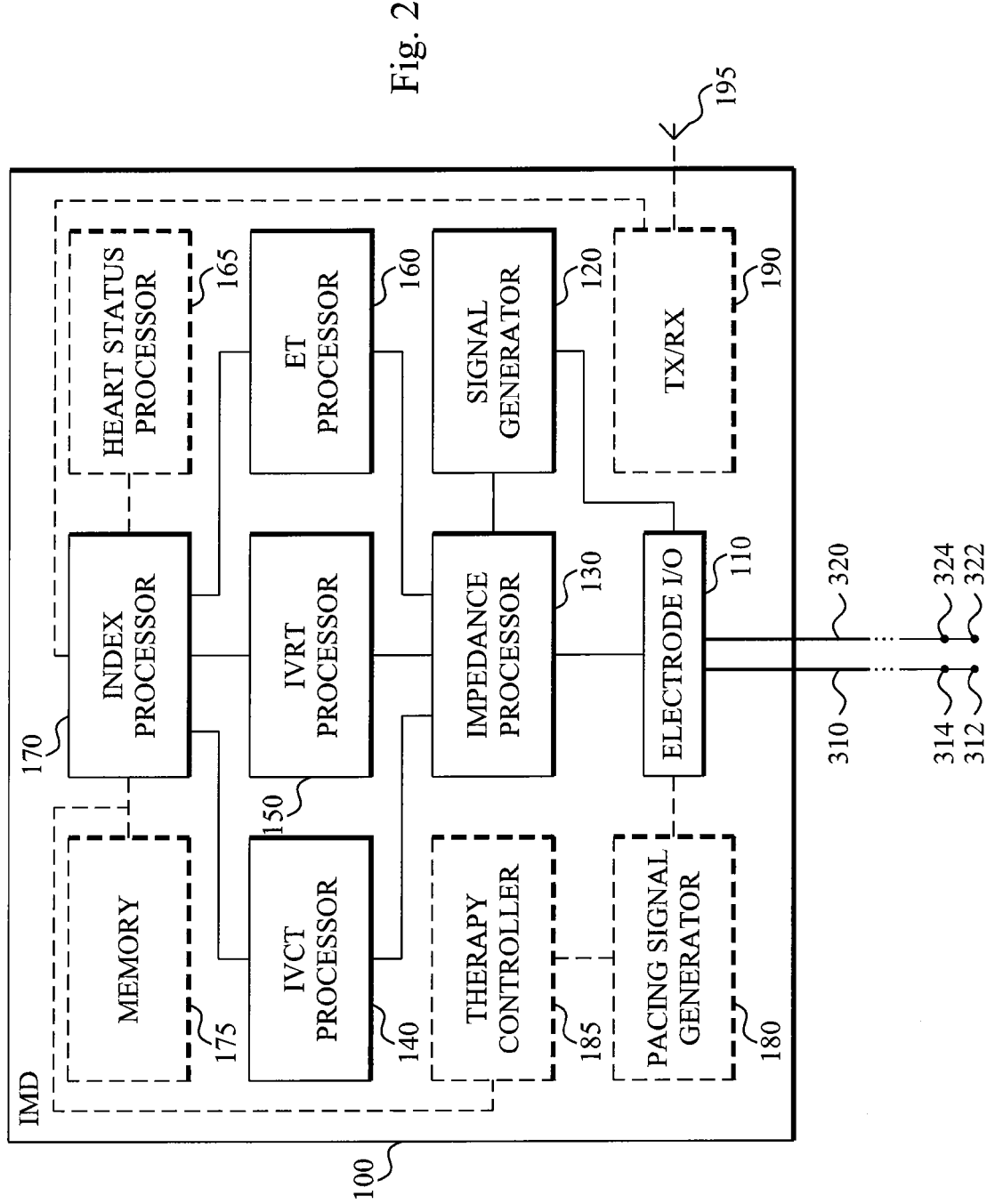
FIG. 2 is a schematic block diagram of an implantable medical device according to an embodiment.

FIG. 2 is a schematic block diagram of an IMD 100 according to the present invention. The IMD 100 comprises an electrode input/output 110 that is, in operation, connectable to multiple electrodes 312, 314, 322, 324 used for applying and sensing electric signals to and from the cardiac tissue of a subject. These electrodes 312, 314, 322, 324 are preferably arranged on one or more implantable medical leads 310, 320 connectable to the IMD 100 through the electrode input 110. As is well known in the art, such an implantable lead or catheter 310, 320 has a proximal end connected to the IMD 100 through the electrode input 110. This IMD-connecting end presents one or more electric terminals that are in electric connection with the electrodes 312, 314, 322, 324 present on the opposite distal lead end, where the electric connection is achieved by electric conductors running along the length of the lead body. The distal lead end with its electrodes 312, 314, 322, 324 is then provided in connection with the heart tissue. For this purpose, the lead 310, 320 can include a tissue anchoring element, such as a helical fixation element, though other fixation elements, such as passive fixation elements, including fines, tines, etc., are also common. The fixation element can indeed constitute one of the electrodes of the lead 310, 320, while remaining electrodes can be ring electrodes (indifferent electrodes), tip electrodes, defibrillation electrode, or the like.

The IMD 100 can be connected to a single medical lead 310, 320, then preferably having at least two electrodes 312, 314, 322, 324. Alternatively, the IMD 100 is connected to multiple, i.e. at least two, implantable leads 310, 320 having electrodes. In either case, the at least one lead 310, 320 can be an intracardiac lead positioned in any of the chambers of the heart, such as right and/or left atrium and/or ventricle. Alternatively, the at least one lead 310, 320 could be epicardially positioned relative the heart. Also a combination of intracardial and epicardial leads is contemplated by the present invention. Furthermore, a subset of the electrodes can instead be provided elsewhere and not on any cardiac lead. For instance, the case of the IMD 100 may constitute one of the electrodes connected to the electrode input 110.

A signal generator 120 of the IMD 100 is electrically connected to the electrode input 110. The generator 120 generates an electric signal, such as a current or voltage signal. The signal is an alternative current (voltage) signal having a particular frequency that is applied to at least a portion of a heart in a subject by two electrodes 312, 322 of the multiple connectable electrodes 312, 314, 322, 324. In operation, the signal generator 120 generates the electric signal having a defined time-dependent voltage profile and forwards the signal to the electrode input 110. The input 110 directs the electric signal to the two signal applying electrodes of which preferably one is provided in connection with or at least close to the subject's heart.

Two electrodes 314, 324 of the multiple connected electrodes 312, 314, 322, 324 collect a resulting electric signal (resulting AC voltage or current signal) originating from the heart tissue. This resulting voltage (current) signal is due to the applied current (voltage) signal from the signal generator 120. In a preferred implementation, the collected signal is a sensed (AC) voltage signal collected using at least two connected electrodes 314, 324.

An impedance processor 130 is electrically connected to the signal generator 120 and the electrode input 110. The processor 130 processes the electric signal (current signal) generated by the signal generator 120 and the resulting electric signal (voltage signal) collected by at least two electrodes 314, 324 connected to the electrode input 110. In more detail, the processor 130 calculates an impedance signal based on the generated and the resulting electric signals.

The impedance processor 130 can utilize different filter combinations, such as bandpass filters, in order to obtain a desired impedance signal based on the measured voltage signal and the applied current signal. The impedance signal determined by the impedance processor 130 can be a complex impedance signal, i.e. comprising a resistive and a reactive component or alternatively an impedance amplitude and phase angle. Alternatively, only the resistive or reactive component or the impedance amplitude is used as impedance signal of the invention.

In a particular embodiment, the impedance processor 130 can determine the impedance signal as an average impedance signal. In such a case, the signal can be the average impedance of the heart determined as the average over multiple successive heart cycles.

An impedance vector is generally employed for identifying the electrodes 312, 314, 322, 324 used for signal application and signal sensing, respectively. As is known in the art, bipolar impedance vectors utilize the same two electrodes for both signal application and signal sensing. In tripolar impedance vectors, the current signal is applied to a tissue over two electrodes and is sensed over two electrodes, one of which but not the other was employed for the signal application. Finally, in quadropolar vectors, two dedicated signal applying electrodes are used and two dedicated different signal sensing electrodes.

Generally bipolar vectors typically give a more local representation of the tissue impedance in the close vicinity to the electrodes. Correspondingly, tripolar and quadropolar vectors could be advantageous when monitoring changes in a tissue present between two medical leads to thereby mainly get an influence of the impedance signal from the intermediate tissue and not other surrounding tissues.

In the present invention, tripolar and in particular quadropolar impedance vectors are preferred even though bipolar vectors may indeed be employed. In a typical quadropolar setting, the IMD 100 is connected to a right ventricular lead 310 (see FIGS. 1 and 2) having at least a first 312 and second 314 electrode. The IMD 100 is also connected to a coronary sinus cardiac lead 320 (or left ventricular lead) having at least a third 322 and fourth 324 electrode. In such a case, the signal generator 120 generates the electric signal to be applied, through the electrode input 110, to at least a portion of the heart using one of the first and second electrodes 312, 314 and one of the third and fourth electrodes 322, 324. The resulting electric signal is then collected by the other of the first and second electrodes 312, 314 and the other of the third and fourth electrodes 322, 324.

The impedance processor 130 is connected to three different processors 140, 150, 160 used by the IMD 100 for determining different time parameters based on the impedance signal. A first processor is an isovolumetric contraction time (IVCT) processor 140 arranged for estimating the IVCT of a heart cycle based on the impedance signal. As is well known in the art, IVCT is defined as the time between the onset of the ventricular contraction (onset of myocardial motion) and the onset of ventricular ejection. This corresponds to the time from the closing of the mitralis valve (often coincides with the R-wave) to the opening of the aortic valve.

Another processor, the isovolumetric relaxation time (IVRT) processor 150 is provided for estimating the IVRT of the heart cycle based on the impedance signal. IVRT corresponds to the period from the closing of the aortic valve to the opening of the mitralis valve.

Furthermore, an ejection time (ET) processor 160 is connected to the impedance processor for estimating the ejection time during the heart cycle based on the impedance signal. ET is defined as the time period between the opening and closing of the aortic valve for the left ventricle. Ejection time could also be defined as the time period when the volume of blood in the left ventricle changes from a maximum value to a minimum value.

The three processors 140, 150, 160 preferably determine the three time parameters based on the impedance signal for one and the same heart cycle. This will give the most correct time data even though it could be possible to, for instance determine one of the time parameters based on the impedance signal for a first heart cycle, determine one other of the parameters based on the impedance signal for a preceding or following heart cycle, etc.

The estimated time parameters are forwarded from the processors 140, 150, 160 to an index processor 170. The index processor 170 determines the Tei-index of the heart cycle based on the provided estimated IVCT, IVRT and ET parameters. In a preferred embodiment, the index processor 170 determines the Tei-index as:

$$\frac{IVCT + IVRT}{ET}$$

The determined Tei-index is of diagnostic and heart performance value and can be used by the IMD 100 for different purposes.

In a first embodiment, the index processor 170 is connected to a memory 175 in the IMD 100. The processor 170 can then forward the calculated Tei-index for storage therein and until further usage. In such a case, the signal generator 120 and impedance processor 130 preferably generate the electric signal and determine the (average) impedance signal at multiple separate time instance, respectively. For instance, the impedance signal can be determined periodically at different pre-defined time intervals per day, week or month. Alternatively, the impedance signal is determined upon a triggering signal generated by some other unit of the IMD 100 or received by an antenna 195 and connected transmitter/receiver (TX/RX) 190 of the IMD 100. The latter case could be realized upon the visit of the IMD patient to his/her physician, which then requests the IMD 100 to initiate a Tei-index determining procedure by sending a triggering signal from the physician's workstation to the receiver 190 of the IMD 100.

In either case, all these Tei-indices determined at different time instances can be stored in the memory 175 for later retrieval. Such a retrieval can be when uploading the determined Tei-indices to the physician's workstation using the transmitter 190 and the connected transmitting antenna 195. The workstation or a connected computer then evaluates the different Tei-indices in order to detect a trend therein that can be indicative of a negative heart condition, such as a heart failure event, or indicative of a (negative or positive) change in myocardial performance.

In an alternative embodiment, the IMD 100 itself comprises such evaluating functionality. Thus, a heart status processor 165 is connected to the index processor 170 and/or the memory 175 and is provided for processing the calculated Tei-indices. This processor 165 uses the Tei-index for generating status data indicative of a current heart status or myocardial performance of the patient. This processing is preferably performed by comparing a determined Tei-index with a threshold value. The threshold value can be a pre-defined value encoded in the IMD 100. Alternatively, the threshold value can be determined by the status processor 165 based on at least one previously determined Tei-index. Thus, the comparison can then be executed by comparing a current Tei-index with a previous Tei-index or with an average of previously calculated Tei-indices.

Generally, the Tei-index should be as low as possible for optimum cardiac performance. A normal value for the Tei-index is therefore around 0.4. Patients suffering from heart failure or some other medical condition or disease negatively affecting the heart performance often have Tei-index close to 1 or even above. The reason for this is that the IVRT and IVCT both increase in, for instance, heart failure due to increased tissue stiffness and lack of contractile myocardial function as a result of the heart failure. This Tei-index increase is further accentuated with lack of synchronization as in patients with left or right bundle branch block. ET generally decreases in heart failure. In summary, the Tei-index is therefore a sensitive marker of left cardiac failure and other conditions negatively affecting the myocardial performance as blood pumping organ.

Thus, if the heart status processor 165 detects a significant change (increase) in Tei-index, diagnostic data representative of the detected negative heart condition is generated. This data can be entered in the memory 175 for later uploading to an external communication unit. Alternatively, or in addition, the data can be directly and wirelessly sent to the external unit using the transmitter 190 of the IMD 100. If the IMD 100 has an alarm unit capable of sounding an alarm signal or providing a tactile alarm signal, such unit could run an alarm if the heart status processor 165 detects a severe deterioration of myocardial performance as determined based on a significant increase in the Tei-index.

A second embodiment uses the Tei-index for adjustment of the device settings, and in particular adjustment or optimization of a pacing therapy scheme employed by the IMD 100 for applying electric treatment pulses to the heart.

The IMD 100 therefore comprises a pacing signal generator 180 connected to the electrode input 110. This generator 180 generating pacing signals, such as resynchronization pacing signal or other electric treatment pacing signals according to a cardiac (resynchronization) therapy scheme. The generated pacing signal is then applied to at least a portion of the heart using two electrodes of the multiple electrodes 312, 314, 322, 324 connected to the electrode input 110.

The pacing signal generator 180 is furthermore connected to a therapy controller, which is also connected to the index processor 170 or memory 175. This controller 185 uses a calculated Tei-index for adjusting the therapy scheme to thereby optimize the applied treatment pacing signal or pulse based on the current cardiac performance. In order to provide an automatic and optimal therapy setting, the IMD 100 is preferably arranged for, following an adjustment of the therapy scheme by the controller 185 and application of the pacing signal based on the updated therapy scheme, estimating an updated Tei-index. This allows the therapy controller 185 to evaluate the previous adjustment and notify if it had any positive or negative effect to the heart performance as reflected by the Tei-index. This procedure can be performed several times to finely adjust the therapy scheme to obtain as optimal heart performance (low Tei-index) as possible. For instance, the optimization procedure can be performed by the IMD 100 until a calculated Tei-index reaches a value that is below an acceptable threshold value.

Different parameters and settings of a therapy scheme can be adjusted in order to reach a more optimal treatment pacing signal. A possible example is to adjust the atrial-to-ventricular (AV) timing delay and/or the ventricle-to-ventricle (VV) timing delay of a cardiac resynchronization therapy scheme. In a typical example, the AV/VV delay is stepped up or down from a starting or default AV/VV delay and the Tei-index is determined following application of the CRT with the new delay value. If the Tei-index improves, further stepping up or down can be performed until the Tei-index once more increases to thereby determine an optimum AV/VV delay. However, if the Tei-index instead increases, the adjustment would then be to step down or up in AV/VV delay until optimum delay value is reached.

A further possibility of adjusting the therapy scheme is to use so-called multi-electrode leads 310, 320. Such a lead 310, 320 has access to multiple different electrodes 312, 314, 322, 324 arranged at different spatial positions along the lead length. The scheme adjustment can then be in form of selecting a new set of two electrodes to use for applying the therapeutic pacing signal to the heart. For instance, if a first multi-electrode lead 310 has access to N electrodes and a second lead 320 has M electrodes, N×M different combinations of inter-lead electrode pairs are possible. If the pacing therapy can also be applied using two electrodes on a same lead, there is in total $$N \times M + \binom{N}{2} + \binom{M}{2}$$

different combinations of two signal applying electrodes in this example. All or a subset of these combinations can be tested and the resulting Tei-index for each combination is determined. Then, the electrode combination resulting in the lowest Tei-index or at least resulting in a Tei-index lower than defining threshold value is selected by the therapy controller.

It is anticipated by the present invention that the therapy controller 185 could adjust the therapy scheme based on the Tei-index by both selecting signal applying electrodes and adjusting AV and/or VV delays or indeed any other therapy scheme parameter.

In another implementation, the therapy controller 185 has access to multiple predefined candidate therapy schemes. Instead of adjusting a single parameter or selecting a particular combination of application electrodes, the controller 185 selects a new candidate scheme among the available ones. In such a case, each of the candidate schemes can be tested for a period of time with the determination of Tei-index after each such trial period. The candidate scheme resulting in the lowest Tei-index is then preferably selected by the controller 185 for use up to a new testing occasion.

The IMD 100 may, for instance, be a biventricular pacemaker having the capability of pacing both ventricles according to a CRT scheme. By pacing both sides of the heart, the pacemaker can resynchronize a heart that does not beat in synchrony, which is common in heart failure patients. In such a case, the IMD 100 is preferably connected to three implantable leads, one in the atrium, such as right atrium, one in the right ventricle and a final one inserted through the coronary sinus to pace the left ventricle. The Tei-index of the invention is highly reflective of any dyssynchrony and also accounts for changes in both diastolic and systolic cardiac performance. Clinical studies (7) have also been conducted indicating that lack of effect on Tei-index is an independent predictor of poor response after CRT. Taken together, Tei-index is therefore well suited for CRT optimization and adjustment in biventricular pacemakers.

Instead of performing the optimization in an automatic manner by the IMD 100, the therapy scheme adjustment can be made by an operator during implantation of the IMD 100 and/or at follow-up visit with the help of the physician's workstation. In such a case, the IMD 100 merely determines Tei-index following different scheme adjustments and upload the indices to the workstation for use by the operator/physician in evaluating the adjusted scheme.

The IMD 100 can optionally include both the therapy controller 185 and the heart status processor 165 that both use the determined Tei-index but for different purposes. In alternative embodiments, the IMD 100 only comprises one or indeed none of these units 165, 185.

The units 110 to 190 of the IMD 100 can be implemented in hardware, software of a combination of hardware and software.

FIG. 3 is a schematic block diagram of an embodiment of the impedance processor 130 of the IMD. The impedance processor 130 comprises a first derivative generator 132 and a second derivative generator 134. The first derivative generator 132 processes the impedance signal determined by the processor 130 and calculates a first time derivative of the impedance signal for at least a portion of a relevant heart cycle. The second derivative generator 134 correspondingly calculates the second time derivative of the impedance signal. These derivative signals are then employed by the IVCT and IVRT processors of the IMD or estimating the IVCT and IVRT parameters, respectively.

The units 132 and 134 of the impedance processor 130 can be implemented in hardware, software of a combination of hardware and software. The units 132 and 134 may all be implemented in the impedance processor 130. In an alternative implementation, at least one of the units 132 and 134 is arranged elsewhere in the IMD.

Figure 4:
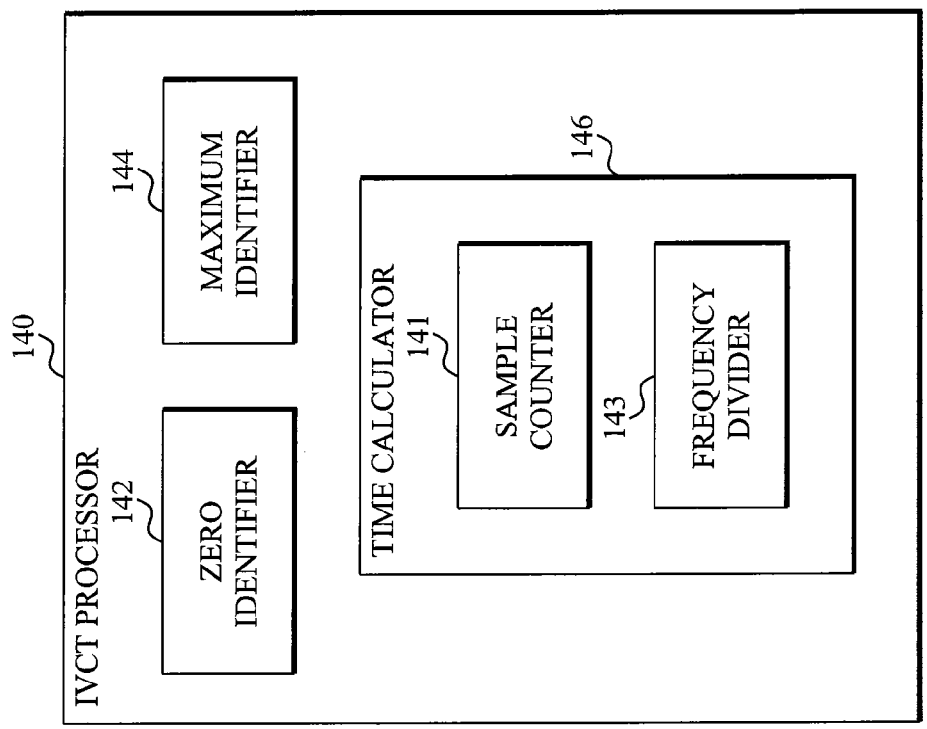
FIG. 4 is a schematic block diagram of an embodiment of the IVCT processor of the implantable medical device in FIG. 2.
Figure 7:
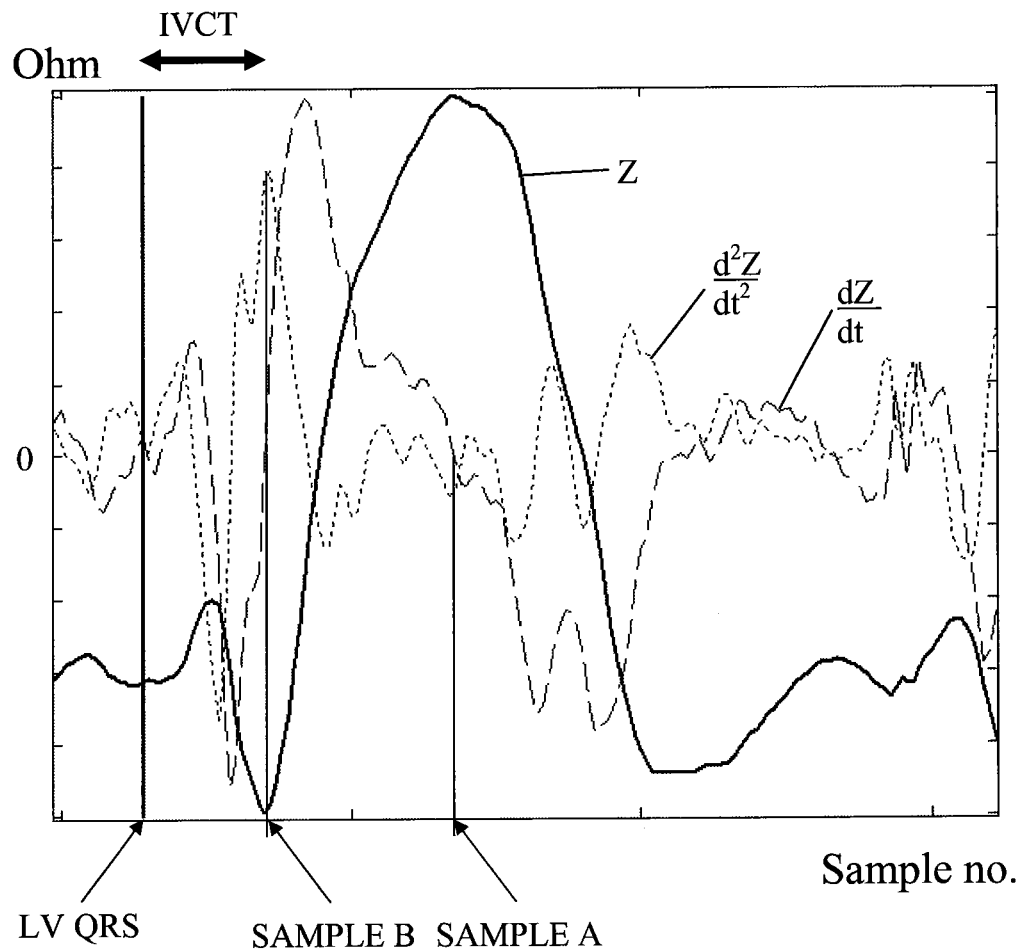
FIG. 7 is a diagram illustrating an embodiment of estimating IVCT from impedance signals.

FIG. 4 is a schematic block diagram of an embodiment of the IVCT processor 140. FIG. 7 is a diagram illustrating the impedance signal (Z), the first time derivative signal $$\left(\frac{dZ}{dt}\right)$$

and the second time derivative $$\left(\frac{d^2Z}{dt^2}\right)$$

of the impedance signal during a heart cycle. With reference to FIGS. 4 and 7, the IVCT processor 140 comprises a zero identifier 142 for processing the first time derivative of the impedance signal. This identifier 142 is employed for identifying the impedance signal sample corresponding to a zero value of the first time derivative following the start of the heart cycle.

In a typical embodiment, the zero identifier 142 passes through the samples containing the first time derivative data from the start of the heart cycle until a zero value sample is located. In this context, the start of heart cycle can be any defined and identifiable event of a heart cycle. A preferred such event corresponds to a characteristic that is identifiable in the impedance signal or in some other signal collected by the IMD. A typical example of a suitable start of the heart cycle is the left ventricular (LV) QRS complex, as indicated in FIG. 7.

Once the zero identifier 142 has located the correct (zero value) first derivative sample it identifies the sample number of the impedance sample coincides in time with located first derivative sample. This sample has been marked as sample A in FIG. 7.

Note that the first derivative sample having zero first time derivative located by the zero identifier 142 must not necessarily be the first zero value first time derivative sample following the start of the heart cycle. In clear contrast and depending on the particular patient, the IMD and the positions of the electrodes used for signal application and collection, the first time derivative may indeed be zero at at least one further occasion following the start of the heart cycle but before the relevant sample A in FIG. 7. In order to locate the correct zero value sample different approaches can be taken.

A first embodiment limits the search among first time derivative occurring close to a clearly identifiable characteristic in the Z, $$\frac{dZ}{dt} \text{ or } \frac{d^2Z}{dt^2}$$

signal. For instance, the global maximum of the impedance signal during the current heart cycle is first identified by the zero identifier 142. The identifier 142 then limits the search for the zero value first time derivative sample among samples close in time to this identified global impedance maximum. For instance, if the global maximum value has sample number S, the search can be limited to the time or sample window encompassing the sample numbers [S−$T_1$, S+$T_1$], where $T_1$ is a defined window-defining value.

In another embodiment, statistics are employed to define a search window relative the start of the heart cycle. Thus, impedance signals collected from multiple different patients can be analyzed in order to identify, given a same sampling frequency, a suitable time or sample window that will encompass the relevant sample having zero first time derivative. In such a case, the search can be limited to the interval [X, X+$T_2$], where X is start-defining value and $T_2$ is a defined window-defining value.

The IVCT processor 140 also includes a maximum identifier 144 employed for processing the second time derivative of the impedance signal. This processor 140 is arranged for identifying the local maximum in the second time derivative signal following the start of the heart cycle but preceding the timing of the sample A identified by the zero identifier 142. In a typical implementation, the maximum identifier 144 first identifies the second time derivative coinciding in time with the sample A identified by the zero identifier 142. The maximum identifier 144 then parses the second time derivative sample backwards in time up to the first sample for the current heart cycle. The identifier 144 then notifies the second time derivative sample having the largest respective second time derivative value. Thereafter, the impedance sample coinciding in time relative the local maximum second time derivative sample is identified. This sample has been marked as sample B in FIG. 7.

A time calculator 146 of the IVCT processor 140 calculates the IVCT parameter as the period of time between the sample B identified by the maximum identifier 144 and the sample coinciding with the start of the heart cycle. In a preferred implementation, the time calculator 146 comprises a sample counter 141 for counting the number of samples between the start of the heart cycle and the sample B. A frequency divider 143 of the time calculator 146 determines the IVCT for the current heart cycle by dividing the counted number of samples with the sampling frequency for the impedance signal. This will give an IVCT parameter defined in seconds, milliseconds or some other time quantity. The period of the heart cycle corresponding to isovolumetric contraction is marked in FIG. 7.

The units 141 to 146 of the IVCT processor 140 can be implemented in hardware, software of a combination of hardware and software. The units 141 to 146 may all be implemented in the IVCT processor 140. In an alternative implementation, at least one of the units 141 to 146 is arranged elsewhere in the IMD.

Figure 5:
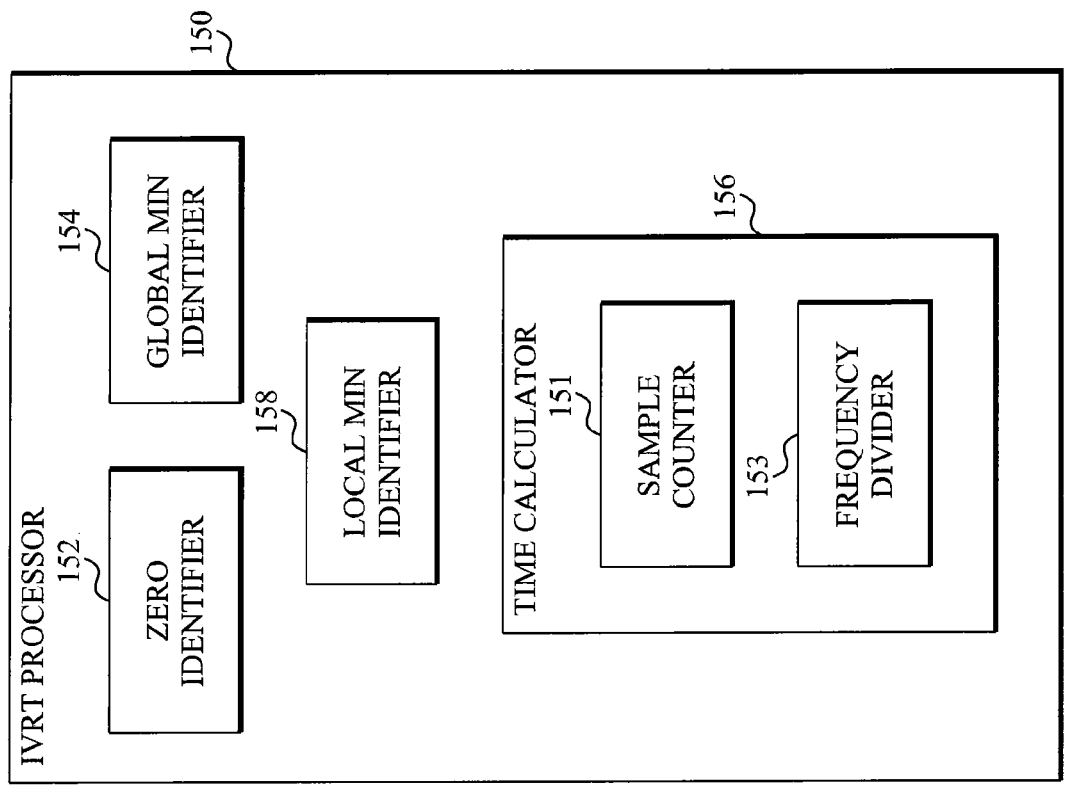
FIG. 5 is a schematic block diagram of an embodiment of the IVRT processor of the implantable medical device in FIG. 2.
Figure 8:
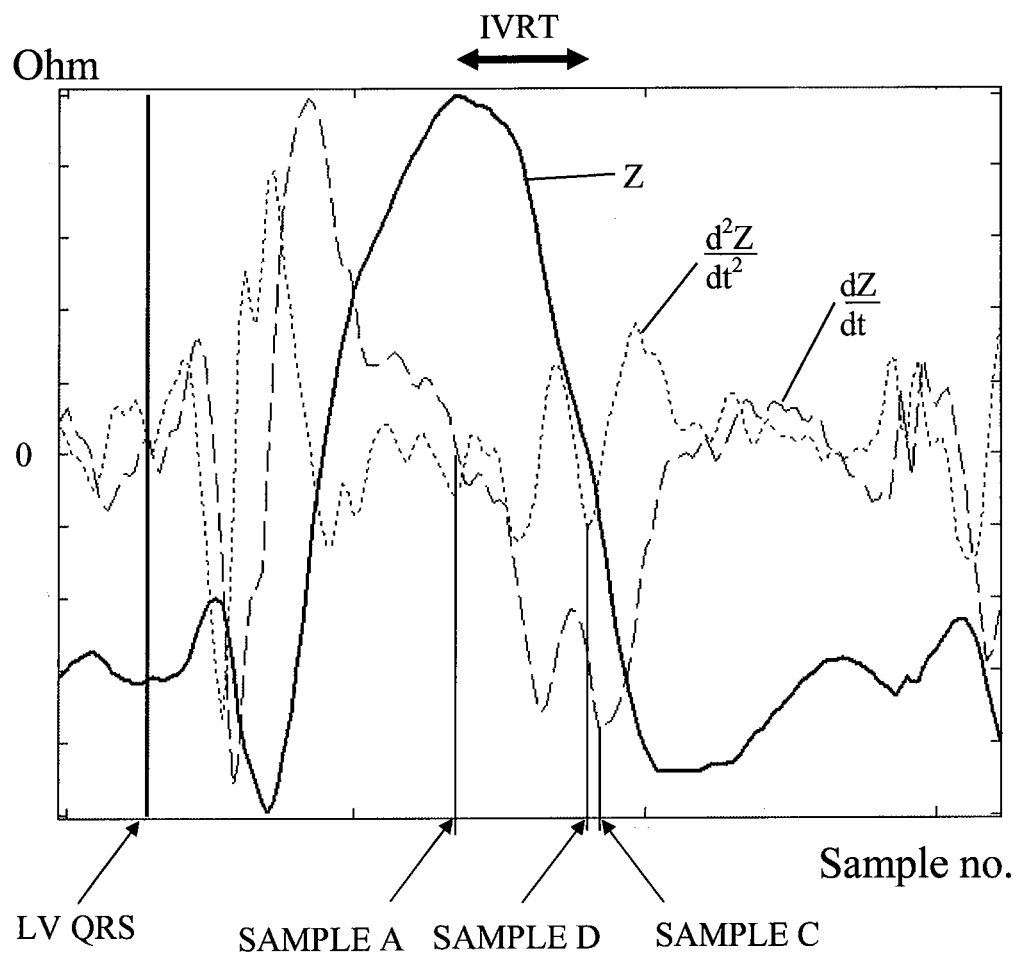
FIG. 8 is a diagram illustrating an embodiment of estimating IVRT from impedance signals.

FIG. 5 is a schematic block diagram of an embodiment of the IVCT processor 140. FIG. 8 is a diagram illustrating the impedance signal (Z), the first time derivative signal $$\left(\frac{dZ}{dt}\right)$$

and the second time derivative $$\left(\frac{d^2Z}{dt^2}\right)$$

of the impedance signal during a heart cycle. With reference to FIGS. 5 and 8, the IVRT processor 150 comprises a zero identifier 152 for processing the first time derivative of the impedance signal. This identifier 152 is employed for identifying the impedance signal sample corresponding to a zero value of the first time derivative following the start of the heart cycle. The operation of this zero identifier 152 is similar to the corresponding zero identifier of the IVCT processor in FIG. 4. The discussion above in connection with the zero identifier of FIG. 4 therefore applies mutatis mutandis to the present zero identifier 152. As a result, the zero identifier 152 identifies the sample A marked in FIG. 8.

The IVRT processor 150 also comprises a global minimum identifier 154 for processing the first time derivative of the impedance signal. The identifier 154 is arranged for identifying a global minimum of the first time derivative occurring after the sample A identified by the zero identifier 152. Thus, the global minimum identifier 154 preferably identifies the first time derivative sample coinciding in time with the sample A. The identifier 154 then parses through the first time derivative samples to the end of the current heart cycle. The sample having the smallest first time derivative value of the parsed samples is identified by the global minimum identifier 154. The impedance sample coinciding in time with this identified sample is marked as sample C in FIG. 8.

A local minimum identifier 158 is provided in the IVRT processor 150 for processing the second time derivative of the impedance signal. The identifier 158 is arranged for identifying a first local minimum in the second time derivative occurring preceding the timing of the sample C identified by the global minimum identifier 154 but occurring following the timing of the sample A identified by the zero identifier 152. The identified minimum is preferably the first minimum of the second time derivative preceding sample C. In a particular embodiment, the local minimum identifier 158 first notifies the sample numbers of the second time derivative sample sequence corresponding in time to sample A and sample C. The identifier 158 then parses the second time derivative samples backwards in time starting from the sample coinciding with sample C. The first sample corresponding to a local minimum in the second time derivative signal is then identified and the corresponding sample of the impedance signal sequence is identified. This sample is marked as sample D in FIG. 8.

The processor 150 also comprises a time calculator 156 arranged for calculating the IVRT parameter as the period of time between sample A and sample D. In a preferred implementation, the time calculator 156 comprises a sample counter 151 for counting the number of samples between the sample A and the sample D. A frequency divider 153 of the time calculator 156 determines the IVRT for the current heart cycle by dividing the counted number of samples with the sampling frequency for the impedance signal. This will give an IVRT parameter defined in seconds, milliseconds or some other time quantity. The period of the heart cycle corresponding to isovolumetric relaxation is marked in FIG. 8.

The units 151 to 158 of the IVRT processor 150 can be implemented in hardware, software of a combination of hardware and software. The units 151 to 158 may all be implemented in the IVRT processor 150. In an alternative implementation, at least one of the units 151 to 158 is arranged elsewhere in the IMD.

Figure 6:
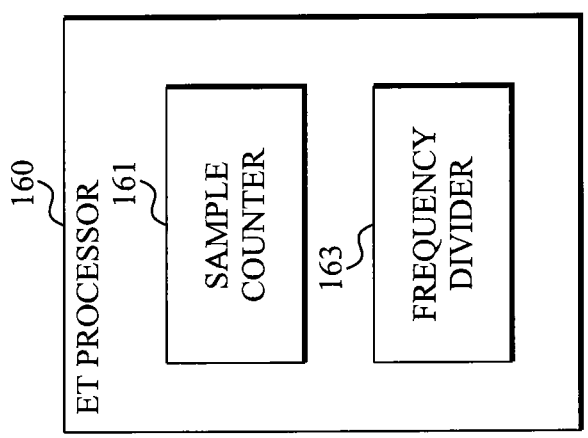
FIG. 6 is a schematic block diagram of an embodiment of the ejection time processor of the implantable medical device in FIG. 2.

FIG. 6 is a schematic block diagram of an embodiment of the ejection time processor 160. The processor 160 preferably comprises a sample counter 161 for counting the number of samples between the sample A and the sample B identified by the zero identifier of the IVRT/IVCT processor and the maximum identifier of the IVCT identifier, respectively. Thus, ET is defined as the period of time from the end of the isovolumetric contraction up to the start of the isovolumetric relaxation in the current heart cycle.

A frequency divider 163 of the ET processor 160 determines the ET for the current heart cycle by dividing the counted number of samples with the sampling frequency for the impedance signal. This will give an ET parameter defined in seconds, milliseconds or some other time quantity.

The units 161 and 163 of the ET processor 160 can be implemented in hardware, software of a combination of hardware and software. The units 161 and 163 may all be implemented in the ET processor 160. In an alternative implementation, at least one of the units 161 and 163 is arranged elsewhere in the IMD.

The above-described units and algorithms for calculating the IVCT, IVRT and ET during a heart cycle are preferred calculation algorithms due to their simplicity and robustness. The present invention is though not limited thereto but can use any other processing of the impedance signal, the first and/or second time derivative of the impedance signal for identifying the relevant isovolumetric contract and relaxation periods and the ejection period.

Figure 9:
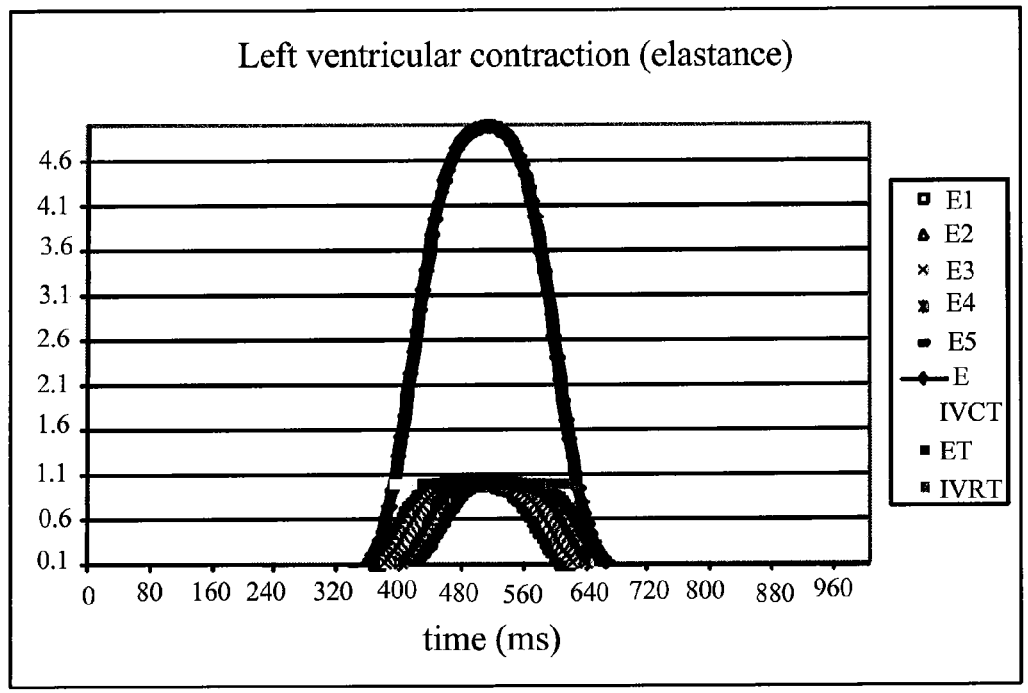
FIG. 9 is a diagram illustrating a simulation of a well synchronized left ventricular contraction and the distribution of IVRT, IVCT and ejection time in the heart cycle.

FIG. 9 is a diagram illustrating an illustration of a well synchronized left ventricular contraction. Five left ventricular segments are illustrated, E1 to E5. The curve E is the sum of the five segments and represents the global LV function. The respective phases, IVCT (about 40 ms), ET (about 210 ms) and IVRT (about 40 ms) are indicated in the figure. The Tei-index for this well-performing heart is 0.38.

Figure 10:
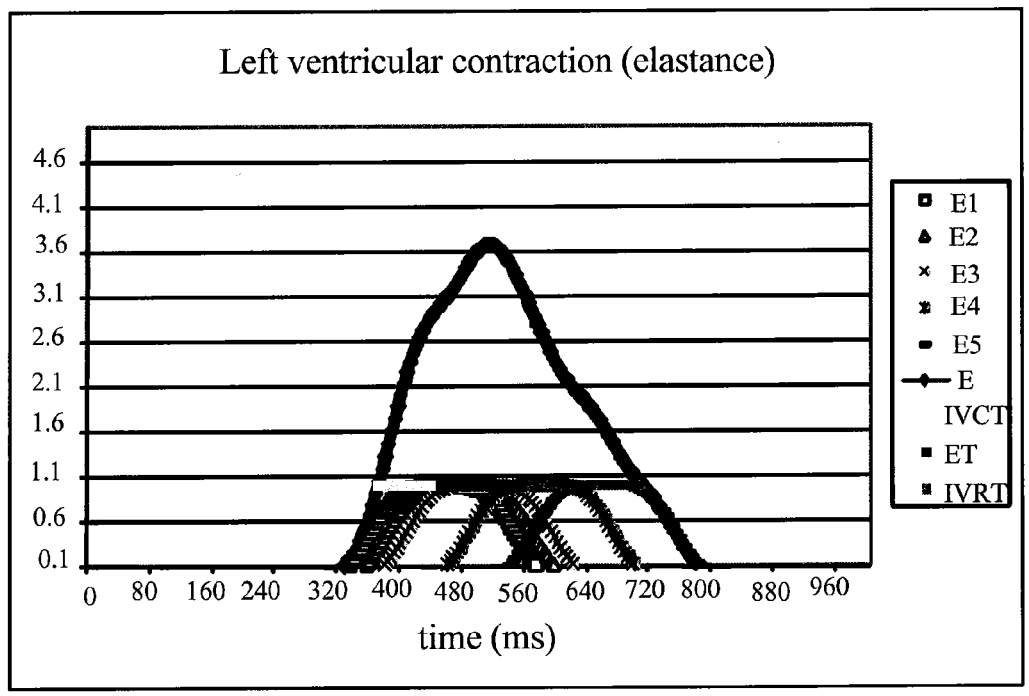
FIG. 10 is a diagram illustrating a simulation of left ventricular contraction with severe dyssynchrony in heart failure and the distribution of IVRT, IVCT and ejection time in the heart cycle.

A corresponding simulation of left ventricular contraction but with severe dyssynchrony in heart failure is illustrated in FIG. 10. As in FIG. 10, five separate left ventricular segments (E1 to E5) and the sum of these segments (E) are illustrated. It is clear from the figure that during this heart failure condition, IVCT is prolonged (about 90 ms), ET is shortened (about 170 ms) and IVRT is prolonged (about 140 ms) as compared to a healthy heart. The resulting Tei-index is significantly increased as compared to the situation illustrated in FIG. 9 and now becomes 1.35.

These simple simulations indicate that the Tei-index is a very sensitive diagnostic parameter this is well suited as representative of the myocardial performance and can therefore be of great value in heart diagnosis and IMD therapy adjustments.

Figures 11, 14:
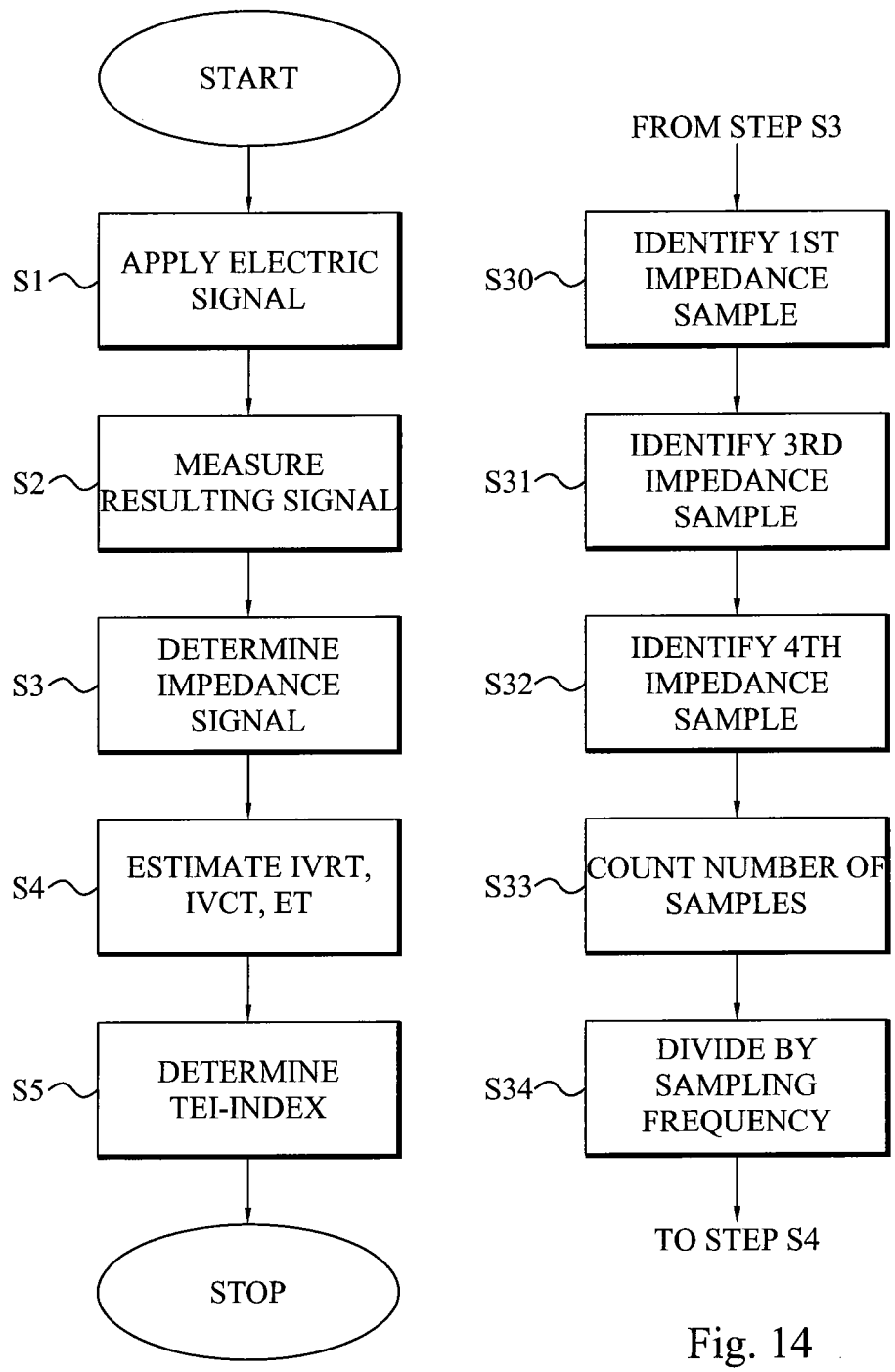
FIG. 11 is a flow diagram illustrating a method of determining a cardiac performance parameter according to the present invention.
FIG. 14 is a flow diagram illustrating additional steps of the method in FIG. 11.

FIG. 11 is a flow diagram illustrating a method for determining a Tei-index for a subject using impedance data. The method starts in step S1, where an electric signal (current or voltage signal) is applied to a least a portion of a heart in the subject using two implantable electrodes. A resulting electric signal (voltage or current signal) is collected or measured from at least a portion of the heart using two implanted electrodes in step S2. As has been discussed herein, the measuring electrodes may be the same as the applying electrodes, one of the electrodes are used for both signal application and collection or dedicated application and collection electrodes are used.

Step S3 determines an impedance signal for at least one heart cycle based on the applied electric signal and the collected resulting signal. The impedance signal can represent the impedance changes of at least a portion of the heart, preferably at least a part of the left ventricle, for one heart cycle. Alternatively, the impedance is determined for multiple successive heart cycles. An average of the impedance during these multiple heart cycle can then be determined in order to compensate for temporary variation in the impedance.

The impedance signal is then processed in step S4 for the purpose of the determining the three time parameters of the invention, i.e. isovolumetric contraction time, isovolumetric relaxation time and ejection time. A next step S5 calculates the Tei-index for the current heart cycle (possibly average heart cycle) based on the estimated IVCT, IVRT and ET. The method then ends.

The procedure for establishing a Tei-index of the invention and illustrated in FIG. 11 can preferably be conducted periodically, such as scheduled at defined time instance(s) per day or week. Alternatively, the procedure may be initiated upon a special triggering event, such as the reception of a request for initiating a Tei-index estimation.

Figure 12:
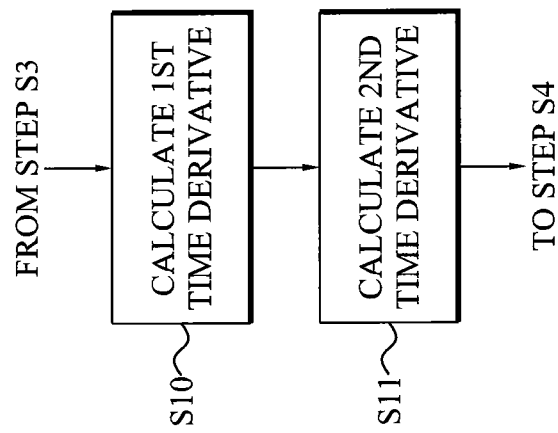
FIG. 12 is a flow diagram illustrating additional steps of the method in FIG. 11.

FIG. 12 is a flow diagram illustrating additional preferred steps of the Tei-index determining method of FIG. 11. The method continues from step S3 of FIG. 11. A next step S10 calculates a first time derivative of the impedance signal for at least a portion of the current heart cycle, preferably during the whole or at least substantially the whole heart cycle. Step S11 correspondingly calculates the second time derivative of the impedance signal for at least a portion of the heart cycle. The estimation of the IVCT and IVRT parameters in step S4 of FIG. 11 is then performed at least partly based on the calculated first and second time derivatives.

Figure 13:
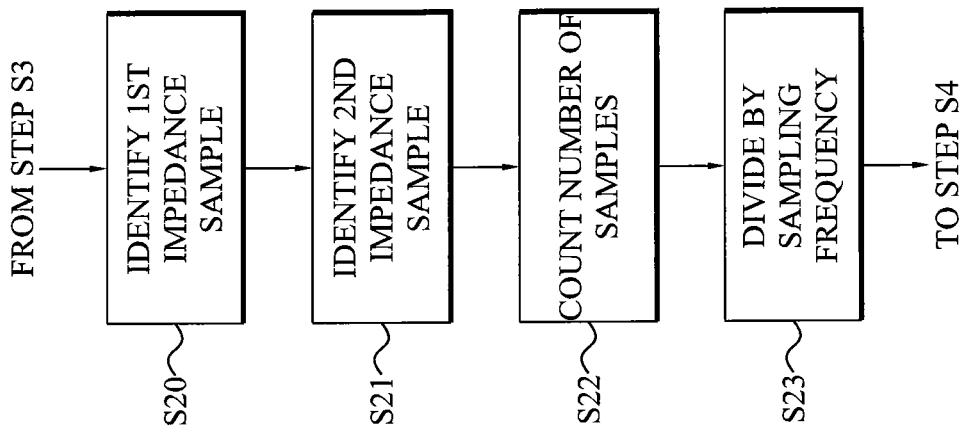
FIG. 13 is a flow diagram illustrating additional steps of the method in FIG. 11.

FIG. 13 is a flow diagram illustrating an embodiment of determining the isovolumetric contraction time based on the impedance signal. The method continues from step S3 of FIG. 11. A next step S20 identifies an impedance signal sample corresponding to a zero value of the first time derivative following the start of the current heart cycle. This step S20 is conducted as previously discussed in connection with FIGS. 4 and 7. A next step S21 identifies an impedance signal sample corresponding to a maximum in the second time derivative following the start of the heart cycle but preceding a timing of the signal sample identified in step S20. The isovolumetric contraction time is then determined as the period of time between the impedance sample identified in step S21 and the start of the heart cycle.

This time is preferably determined by counting, in step S22, the number of samples between the start of the heart cycle and the sample identified in step S21. Step S23 divides the counted number of samples with the sampling frequency of the impedance signal in order to get the IVCT parameter expressed in the time domain (seconds or milliseconds). The method then continues to step S4 of FIG. 11 for calculating the remaining two time parameters.

FIG. 14 is a flow diagram illustrating an embodiment of determining the isovolumetric relaxation time based on the impedance signal. The method continues from step S3 of FIG. 11. A next step S30 identifies an impedance signal sample corresponding to a zero value of the first time derivative following the start of the current heart cycle. This step S30 is conducted similar to step S20 of FIG. 13. Step S31 identifies a sample corresponding to a global minimum of the first time derivative following the sample identified in step S30. An impedance signal sample coinciding with a first local minimum of the second time derivative preceding the timing of the sample identified in step S31 but following the timing of the sample identified in step S30 is identified in step S32. The isovolumetric relaxation time is then defined as the period of time between the samples identified in steps S30 and S32.

This time is preferably determined by counting, in step S33, the number of samples between the samples identified in step S30 and S32. Step S34 divides the counted number of samples with the sampling frequency of the impedance signal in order to get the IVRT parameter expressed in the time domain (seconds or milliseconds). The method then continues to step S4 of FIG. 11 for calculating the remaining two time parameters.

The calculation of the IVRT and IVCT parameters can be performed sequentially or in parallel.

Ejection time is then defined as the period of time from the end of IVCT up to the start of IVRT. ET can be determined by counting the number of samples between the sample identified in step S30 of FIG. 14 or step S20 of FIG. 13 and the sample identified in step S21 of FIG. 14. The counted number of samples is divided by the sampling frequency of the impedance signal in order to get the ET parameter expressed in the time domain (seconds or milliseconds).

Figure 15:
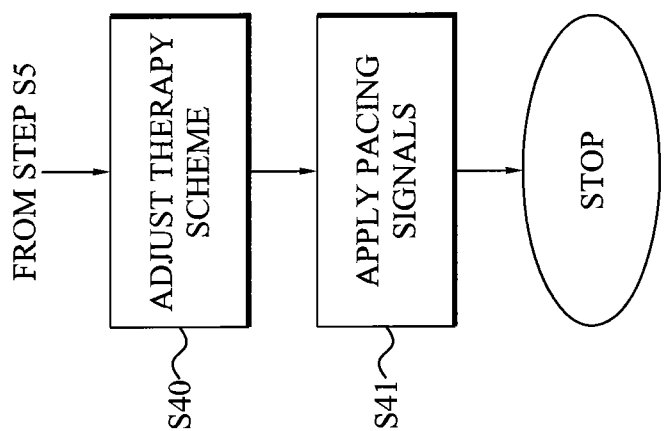
FIG. 15 is a flow diagram illustrating additional steps of the method in FIG. 11.

\FIG. 15 is a flow diagram illustrating a particular use of the Tei-index determined according to the invention. The method continues from step S5 of FIG. 11. A next step S40 adjusts a cardiac therapy scheme, such as a cardiac resynchronization therapy scheme, based on the calculated Tei-index. This adjustment can, for instance, be realized as an adjustment of the AV and/or VV timing delay of applied pacing pulses. Another possible realization is the change of electrode pair used for applying the therapy pacing signal. A further example is the change of a current therapy scheme to one out of multiple available predefined candidate schemes from a scheme library.

A next step S41 applies pacing signal to at least a portion of the heart according to the adjusted therapy scheme. In a preferred embodiment, a new Tei-index calculation procedure is preferably initiated following a time period after application of the adjusted therapy scheme. This allows evaluation of whether the new scheme resulted in an improvement in cardiac performance (reduction in Tei-index) or a deterioration of the performance (increase in Tei-index). An iterative scheme adjustment procedure can then be conducted with Tei-index-dependent evaluation of the adjusted scheme in order to identify a therapy scheme that is optimal or at least suited for the current condition of the patient's heart.

Figure 16:
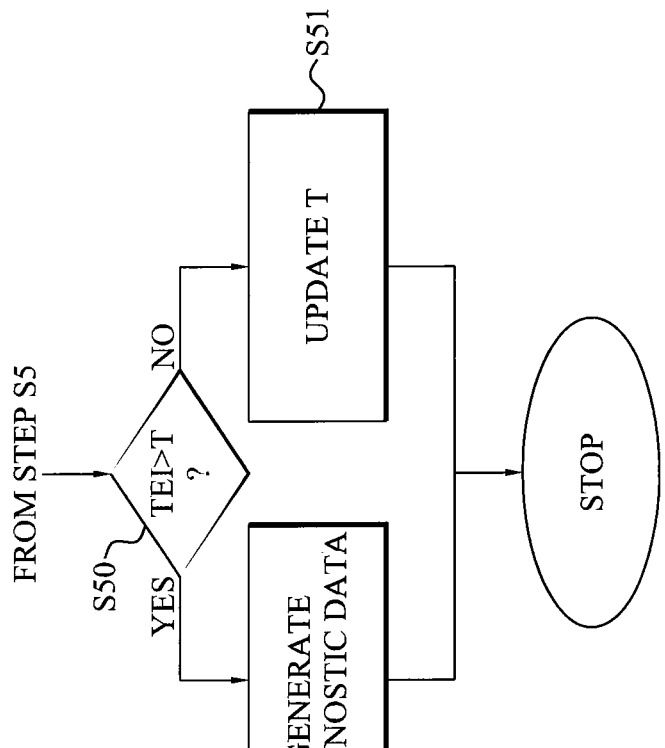
FIG. 16 is a flow diagram illustrating additional steps of the method in FIG. 11.

FIG. 16 is a flow diagram illustrating another possible implementation of the Tei-index determined according to the present invention. The method continues from step S5 of FIG. 11. A next step S50 compares the calculated Tei-index with a threshold value. The threshold can be a predefined value but is preferably an average value of previously calculated Tei-indices. If the Tei-index is lower than the threshold, the method continues to step S51, where the threshold value is preferably updated based on the newly determined Tei-index. The method then ends or returns to step S1 for the purpose of initiating a new Tei-index determination.

If, however, the Tei-index is larger than the threshold this is an indication of deterioration in the cardiac performance and is of diagnostic value. Diagnostic data representative of the detected (unfavorable) heart condition is generated in step S52 based on the comparison of step S50. The diagnostic data may be stored in the IMD for later retrieval or could be sent directly to an external communication unit. Furthermore, if the Tei-index is significantly higher than the threshold, an alarm may be run such as an audio and/or tactile alarm notifying the patient of the detected cardiac condition.

Although modifications and changes may be suggested by those skilled in the art, it is the intention of the inventors to embody within the patent warranted heron all changes and modifications as reasonably and properly come within the scope of their contribution to the art.

What is claimed is:

1. A method for determining a Tei-index of a subject comprising: applying an electric signal to at least a portion of a heart in said subject by two implanted electrodes; measuring a resulting electric signal from at least a portion of said heart collected by two implanted electrodes; determining an impedance signal based on said electric signal and said resulting electric signal; estimating an isovolumetric relaxation time of a heart cycle based on said impedance signal; estimating an isovolumetric contraction time of said heart cycle based on said impedance signal; estimating an election time of said heart cycle based on said impedance signal; determining a Tei-index of said heart based on said estimated isovolumetric relaxation time, said estimated isovolumetric contraction time and said ejection time; calculating a first time derivative of said impedance signal for at least a portion of said heart cycle; and calculating a second time derivative of said impedance signal for at least a portion of said heart cycle, wherein said determining said isovolumetric relaxation time and said isovolumetric contraction time are performed at least partly based on said first and second time derivatives of said impedance signal.

2. The method according to claim 1, further comprising: adjusting a cardiac therapy scheme based on said Tei-index; and applying therapy pacing signals according to said adjusted cardiac therapy scheme to at least a portion of said heart by two implantable electrodes.

3. The method according to claim 2, wherein said adjusting comprises adjusting at least one of an atria-to-ventricle timing delay and a ventricle-to-ventricle timing delay of said cardiac therapy scheme based on said Tei-index.

4. The method according to claim 2, wherein said adjusting step comprises selecting, based on said Tei-index, an electrode of multiple electrodes of a multi-electrode lead (310; 320) for applying said therapy pacing signals.

5. The method according to claim 1, wherein said determining said isovolumetric contraction time comprises: identifying a first impedance signal sample corresponding to a zero value of said first time derivative of said impedance signal following a start of said heart cycle; identifying a second impedance signal sample corresponding to a largest value of said second time derivative of said impedance signal following said start of said heart cycle but preceding a timing of said first impedance signal sample; and calculating said isovolumetric contraction time as a period of time between second impedance signal sample and said start of said heart cycle.

6. The method according to claim 5, wherein said determining said ejection time comprises: counting a number of samples between said first impedance signal sample and said second impedance signal sample; and calculating said ejection time based on a division of said counted number of samples and a sampling frequency of said impedance signal.

7. The method according to claim 1, wherein said determining said isovolumetric relaxation time comprises: identifying a first impedance signal sample corresponding to a zero value of said first time derivative of said impedance signal following a start of said heart cycle; identifying a third impedance signal sample corresponding to a global minimum of said first derivative of said impedance signal following a timing of said first impedance signal sample; identifying a fourth impedance signal sample corresponding to a first local minimum of said second time derivative of said impedance signal preceding a timing of said third impedance signal sample but following a timing of said first impedance signal sample; and calculating said isovolumetric relaxation time as a period of time between said first impedance signal sample and said fourth impedance signal sample.

8. The method according to claim 1, further comprising generating status data indicative of a current heart status of said subject based on said Tei-index.

* * * * *